United States Patent [19]

Kobal

[11] Patent Number: 4,681,121
[45] Date of Patent: Jul. 21, 1987

[54] PROCESS FOR MEASURING SENSORY QUALITIES AND APPARATUS THEREFOR

[76] Inventor: Gerd Kobal, Marquardsenstrasse 9, 8520 Erlangen, Fed. Rep. of Germany

[21] Appl. No.: 819,174

[22] Filed: Jan. 15, 1986

[30] Foreign Application Priority Data

Jan. 15, 1985 [DE] Fed. Rep. of Germany ....... 3501095

[51] Int. Cl.⁴ ............................................ A61M 17/00
[52] U.S. Cl. ................................ 128/731; 128/203.14; 128/203.25
[58] Field of Search ................................. 128/731–732, 128/203.12–203.14, 203.18, 203.22, 205.16, 23–25; 137/606–607, 896–898; 138/26, 30–31, 46

[56] References Cited

U.S. PATENT DOCUMENTS

| | | | |
|---|---|---|---|
| 2,208,633 | 7/1940 | Heidbrink | 128/203.13 X |
| 3,513,834 | 5/1970 | Suzuki et al. | 128/731 |
| 4,127,121 | 11/1978 | Westenskow et al. | 128/203.14 |
| 4,328,823 | 5/1982 | Schreiber | 128/203.14 X |
| 4,533,346 | 8/1985 | Cosgrove, Jr. et al. | 128/731 X |
| 4,576,159 | 3/1986 | Hahn et al. | 128/203.14 |

FOREIGN PATENT DOCUMENTS 2113846 8/1983 United Kingdom ................ 128/731

Primary Examiner—Kyle L. Howell
Assistant Examiner—Angela D. Sykes
Attorney, Agent, or Firm—Walter Ottesen

[57] ABSTRACT

An apparatus is disclosed for measuring sensory qualities, in particular for the measurement of analgesia in the monitoring of anaesthesia, in which substances in gas or vapor form which trigger the specific stimulus are passed in pulse form over the nasal mucosa by a stimulating device and electrical signals correlated with the stimulus are derived from the electro-encephalogram by means of a recording mechanism and analyzed as measured values, is to be improved with regard to the exclusion of interference values. According to the invention, this is achieved by causing the switching device to produce a continuous sequence of pulses and the assessment to be carried out by the assessment unit in an assessment window, the width of which corresponds with a predetermined number of stimulus pulses, it being possible to displace the assessment window over the number of stored signals. In addition, an advantageous process for the control of anaesthesia is described, which consists of a painful nasal stimulus being applied periodically and the response signals being derived from the EEG as measured or control quantities.

7 Claims, 1 Drawing Figure

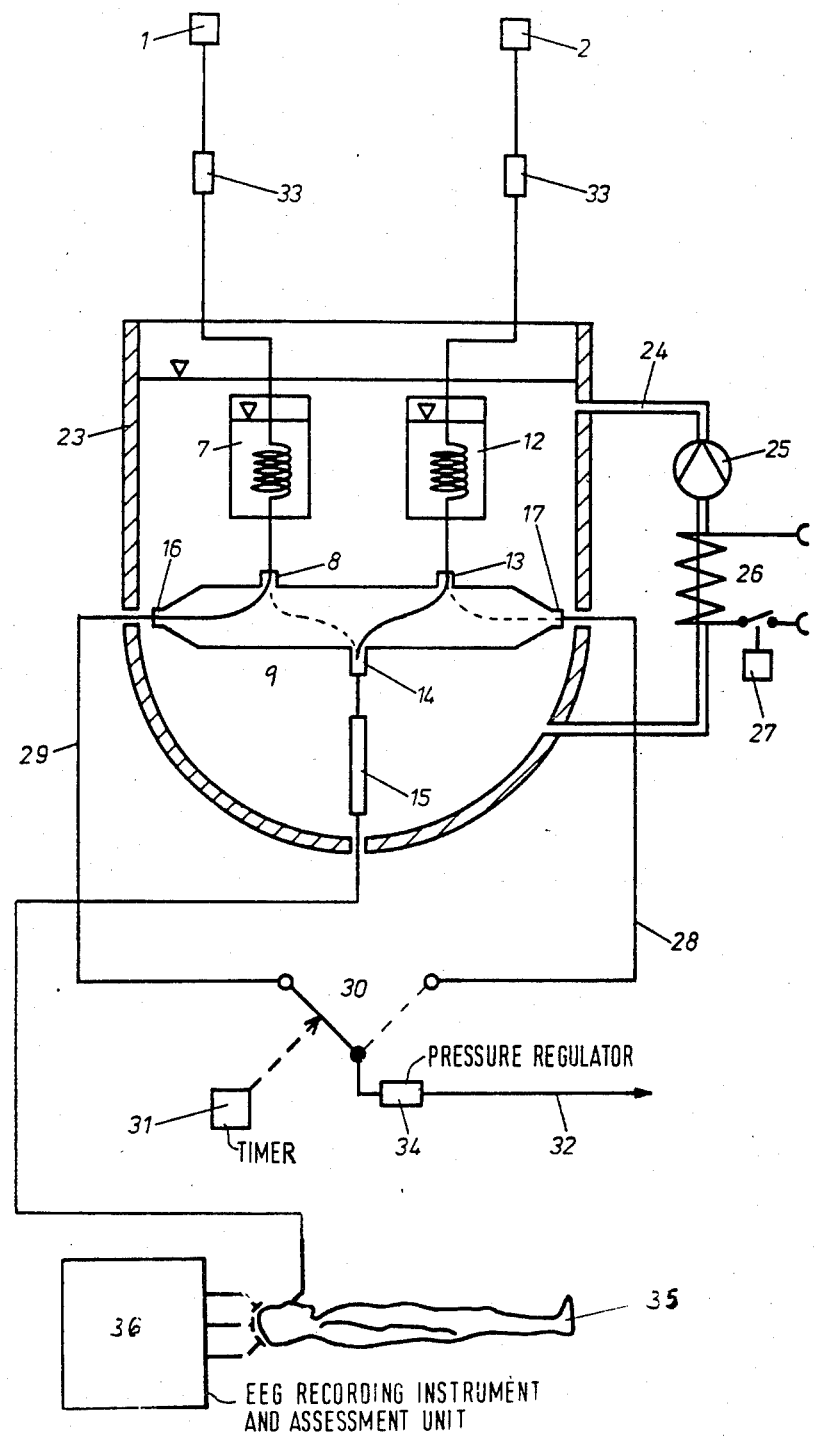

PROCESS FOR MEASURING SENSORY QUALITIES AND APPARATUS THEREFOR

FIELD OF THE INVENTION

The invention relates to a process for measuring sensory qualities, in particular, for measuring analgesia in the monitoring of anaesthesia. In this process, substances in the form of gas or vapor, which trigger the specific stimulus, are passed in pulse form over the nasal mucosa by a stimulating device and electrical signals correlated with the stimulus are derived from the electro-encephalogram by means of a recording mechanism and analyzed as measured values in an assessment unit. The merging of stimulus pulses into a stream of neutral gas or vapor is carried out by means of a switching device and the stream of neutral gas or vapor is kept constant with regard to the flow characteristics. An appropriate apparatus for carrying out the process is also described.

BACKGROUND OF THE INVENTION

In the paper by G. Kobal and K. H. Plattig in the journal "Zeitschrift für Elektro-Encephalograhie, Elektromyographie und verwandte Gebiete" (Journal of electro-encephalography, electro-myography and related fields), 9 (1978) pages 135 to 145, investigations are described in which the sensory quality. of smell can be checked by causing a test substance introduced nasally via a nasal probe to trigger a stimulus, which can be revealed in the electro-encephalogram (EEG).

In tests of this kind it is important to introduce the test substance, which is conveyed into the nose in gas or vapor form, in such a way that the expected stimulus depends only on the test substance and not on other changes, for example on changes in the flow rates or temperature values of the introduced gas or vapor. Because of the sensitivity of the encephalographic response to such stimuli, reliable measurement is possible only when one has succeeded in applying specific stimuli and excluding unwanted stimulating influences. The encephalogram can generally be assessed with the help of a computer.

SUMMARY OF THE INVENTION

The invention is based on the need to describe a process by means of which the above-mentioned measurement of sensory qualities can be advantageously carried out in such a way that monitoring of the stimulus-correlated electrical signals is possible over a predetermined period of time of any length.

This task is solved with a process of the kind described above by a continuous sequence of pulses being produced by the changeover device and the assessment being carried out by the assessment unit in an assessment window, the width of which corresponds with a predetermined number of stimulus pulses, it being possible to displace the assessment window over the number of stored signals. If the flow of gas or vapor conveyed to the nasal mucosa has constant flow characteristics, particularly with regard to flow rate, temperature and water vapor saturation, it can be assumed that the stimulus-correlated electrical signals occurring in the EEG are derived exclusively from the introduced stimulus substance.

Such a process can be particularly advantageously used for the measurement or continuous monitoring of adequate analgesia, which must be aimed at if optimum operating conditions are to be achieved. Even in modern anaesthesia the dosage of the anaesthetic is still largely carried out on the basis of visual impressions or general changes in circulation. In these circumstances, however, it is impossible to distinguish with certainty whether a given reaction by the patient is an indication of insufficient analgesia, inadequate vegetative stabilization or that he is still conscious.

An advantageous new method for monitoring analgesia during anaesthesia consists of applying a continuous painful nasal stimulus to the nasal mucosa and regulating the supply and/or concentration of the anaesthetic substance in such a way that the EEG signals produce a corresponding pattern, which indicates adequate analgesia on the basis of preliminary comparative tests.

Another application of the process described above is in the investigation of the senses of smell and taste using one or more substances which are introduced nasally and orally in the form of a test gas. With this method, the investigation can be carried out objectively and independently of the will of the patient by means of EEG signal values. This is of particular importance if the patient is unable or unwilling to make a constructive contribution to the progress of the investigation.

According to the invention, the stimulus-correlated signals are analyzed and stored in the assessment unit. The assessment takes the form of the stimulus-correlated electrical signals, which appear as the response to the continuous sequence of pulses, being evaluated in an assessment window, which is predetermined by a window comparator. In so doing, the assessment window moves over the signal sequence in such a way that the most recently occurring number of electrical signals always appears within the assessment window. The assessment window has a most appropriate width of 10 signals. From this group of signals the determining measured value is established in each instance in a manner described, for example, in a different context for studies of the human sense of smell in: G. Kobal, "Elektrophysiologische Untersuchungen des menschlichen Geruchssinnes" (Electro-physiological studies of the human sense of smell), Thieme Stuttgart, New York: Thieme, 1981, page 24.

The assessment window is moved over the contents of the memory, only those signals detected by the assessment window being evaluated. In this way it is also possible to monitor the progress of the analgesia, using all the stored signals, in retrospect from start to finish.

By means of the features of the invention described, a process is provided for sensory investigation or monitoring, in which a specific stimulus response can be derived from the EEG with the exclusion of most of the interfering factors; this can be advantageously used to control an anaesthetic apparatus.

An already known apparatus for carrying out the process of measuring sensory qualities incorporates a rerouting chamber, which contains inlets for neutral gas and stimulus gas and an outlet to the supply line to the nose. The rerouting chamber can be connected on both sides by means of waste-gas connections to waste-gas lines, which can be connected alternatively to a discharge line via a changeover valve, the inlets and waste-gas connections being arranged in such a way that streams of neutral gas and stimulus gas are produced in the free interior of the rerouting chamber, which move back and forth between the inlet and the waste-gas connection allocated to it and the outlet to the supply line to the nose, depending on the setting of the changeover valve. Because aspiration takes place either on the side of the inlet for neutral gas or on the side of the inlet for stimulus gas, flow conditions are created which allow a rapid changeover between the neutral gas and the interpolated pulses of stimulus gas, without the flow pattern in the outlet to the supply line to the nose being affected.

In order to obtain a steep-gradient rise in the stimulus pulses, it is proposed that a pressure regulator be located in the discharge line and that the changeover valve be designed in such a way that the alternate connection, which is outside of the gas line to the pressure regulator, is blocked. A capillary tube is most advantageously used as the pressure regulator.

The changeover valve can be advantageously constructed so that during the changeover process the total of the partial flows of neutral gas and stimulus gas transmitted during the transitional stage is always equal to the gas flow transmitted in the final positions. In this way fluctuations in the flow are avoided which could be passed on into the supply line to the nose and produce a non-specific stimulus there.

In order to produce the appropriate mixing ratio of stimulus gas and neutral gas, various well known gas mixing devices can be used. The most suitable appears to be the use of capillary tubes supplied at a constant advance pressure. A capillary pipe may also be usefully interposed in the supply line to the nose to obtain a constant discharge flow.

BRIEF DESCRIPTION OF THE DRAWING

The drawing is a schematic of an embodiment of the apparatus according to the invention for carrying out the process of measuring sensory qualities.

DESCRIPTION OF THE PREFERRED EMBODIMENTS OF THE INENTION

Reference numerals 1 and 2 indicate connections for $CO_2$ and compressed air from, for example, suitable steel cylinders.

In order to meter the stimulus gas from its constituents compressed air and $CO_2$, both gases are passed through capillary tubes 33 of differing widths to humidifiers 7, 12.

In a water-filled chamber impervious to overpressure, the humidifiers 7, 12 contain a microporous pipe which allows water vapor to penetrate through its walls. The outlet of the first air humidifier 7 is connected to an inlet 8 for stimulus gas, which is located in the cylindrical wall of a mixing tube 9.

The outlet of the second air humidifier 12 also leads to an inlet 13 for neutral gas located in the cylindrical wall of the mixing tube 9.

The inlets 8, 13 are positioned symmetrically to an outlet 14, which leads via an interposed capillary tube 15 to a connection for the nasal probe fitted to the patient 35 for transmitting the stimulating pulses to the latter. Block 36 is a schematic representation of the EEG recording instrument and assessment unit.

The two ends of the mixing tube 9 are provided with waste-gas connections 16, 17, which can be connected alternately via waste-gas lines 28, 29 to a pressure regulator 34.

The mixing tube 9, the two air humidifiers 7, 12 and the capillary tube 15 are housed in a water-bath thermostat 23, which can be adjusted to a constant water temperature, that is, to body temperature, by means of a circulating conduit system 24, a feed pump 25 and a heating coil 26 having a switching mechanism 27. The heating system consists of a conventional electric heating system which is connected to a power supply. The layout of the associated regulating system corresponds to already known designs.

The alternate connection of the two waste-gas lines 28, 29 to the pressure regulator 34 is made via a changeover valve 30, which is actuated by a timer 31 acting in accordance with the desired pulse length and pulse sequence frequency.

In the setting of the changeover valve 30 illustrated, the pressure regulator 34 is connected to the waste-gas connection 16 via the waste-gas line 29, so that the stimulus gas component (shown by a dashed line in the drawing in the mixing tube 9) is extracted, while the neutral gas component (shown as a solid line in the mixing tube 9) passes to the outlet 14. When the changeover valve 30 is switched to the other end position, the flow conditions are reversed, and stimulus gas is then supplied to the outlet 14. Depending on the dimensions of the capillary tubes 33, however, some of the neutral gas component is also added to the stimulus gas component, so that a mixture of both components produced in the mixing tube 9 determines the concentration of the stimulus gas to be supplied to the nasal probe.

It is understood that the foregoing description is that of the preferred embodiment of the invention and that various changes and modifications may be made thereto without departing from the spirit and scope of the invention as defined in the appended claims.

What is claimed is:

1. Method for measuring sensory qualities such as for measuring analgesia while monitoring anaesthesia on a patient, the method comprising the steps of:
    passing stimulating pulses of vaporous or gaseous substances by means of a stimulating device over the nasal mucosa for triggering a specific stimulus;
    said stimulating pulses being connected in series in a neutral vaporous or gaseous flow by means of a switching device thereby generating a continuous sequence of pulses with rapid changeover between the neutral vaporous or gaseous flow and the interpolated stimulating pulses, said flow being kept constant with respect to the flow characteristics thereof;
    deriving stimulus correlated electrical signals from the electro-encephalogram of the patient by means of a recording instrument; and,
    analyzing and storing said electrical signals as measured quantities in an assessment unit, said electrical signals being analyzed in an assessment window having a width corresponding to a predetermined number of said stimulating pulses and said assessment window being displaceable over the number of signals stored in said assessment unit.

2. The method of claim 1, wherein the supply of anaesthetic gas is controlled by applying a painful vaporous or gaseous stimulus to the nasal mucosa at intervals and deriving response signals in the form of measured or control quantities from said electro-encephalogram.

3. Apparatus for carrying out a method for measuring sensory qualities such as for measuring analgesia while monitoring anaesthesia on a patient, the apparatus comprising:
    first gas supply means for supplying a stimulus gas;
    second gas supply means for supplying a neutral gas;

a chamber having two inlets for receiving said stimulus gas and said neutral gas, respectively;

an outlet adapted to communicate with the nasal mucosa of the patient;

said chamber having waste-gas connections at respective ends thereof;

a discharge conduit;

a pressure regulator mounted in said discharge conduit;

a changeover valve movable between two positions for selectively connecting one of said waste-gas connections to said discharge conduit while at the same time blocking the other one of said waste-gas connections; and, said inlets and said waste-gas connections being arranged in said chamber so as to cause respective flows of stimulus gas and neutral gas to develop in said chamber and so as to cause each of said flows to be rerouted in dependence upon the position of said valve along a first path between the inlet corresponding to the flow and the waste-gas connection corresponding thereto on the one hand and along a second path between the inlet corresponding to the flow and said outlet on the other hand.

4. The apparatus of claim 3, said pressure regulator being a capillary length for setting the quantity flowing therethrough.

5. The apparatus of claim 3, said changeover valve being configured so that the flows developing during the movement between said positions is equal to the total flow occurring when said changeover valve is in said positions.

6. The apparatus of claim 3, said first gas supply means and said second gas supply means having respective capillary lengths for supplying corresponding ones of said inlets with said gases at a constant advance pressure so as to determine the mixing ratio in said chamber.

7. The apparatus of claim 6, comprising a further capillary length connected to said outlet of said chamber.

* * * * *